US012213769B2

(12) United States Patent
Watanabe (10) Patent No.: US 12,213,769 B2
(45) Date of Patent: Feb. 4, 2025

(54) ELECTRONIC DEVICE, CONTROL METHOD, AND CONTROL PROGRAM

(71) Applicant: KYOCERA Corporation, Kyoto (JP)

(72) Inventor: Takahiro Watanabe, Yokohama (JP)

(73) Assignee: KYOCERA Corporation, Kyoto (JP)

( * ) Notice: Subject to any disclaimer, the term of this patent is extended or adjusted under 35 U.S.C. 154(b) by 858 days.

(21) Appl. No.: 17/260,027

(22) PCT Filed: Aug. 4, 2020

(86) PCT No.: PCT/JP2020/029908
§ 371 (c)(1),
(2) Date: Jan. 13, 2021

(87) PCT Pub. No.: WO2021/025038
PCT Pub. Date: Feb. 11, 2021

(65) Prior Publication Data
US 2021/0196136 A1 Jul. 1, 2021

(30) Foreign Application Priority Data

Aug. 8, 2019 (JP) .................................. 2019-146594

(51) Int. Cl.
*A61B 5/026* (2006.01)
*A61B 5/00* (2006.01)
*A61B 5/0245* (2006.01)

(52) U.S. Cl.
CPC .......... *A61B 5/0261* (2013.01); *A61B 5/0245* (2013.01); *A61B 5/6817* (2013.01)

(58) Field of Classification Search
CPC ... A61B 5/0261; A61B 5/0245; A61B 5/6817; A61B 5/746; A61B 5/4809; A61B 5/7221
See application file for complete search history.

(56) References Cited

U.S. PATENT DOCUMENTS

| | | | |
|---|---|---|---|
| 10,092,442 B2 | 10/2018 | Aarestad et al. | |
| 2014/0305733 A1* | 10/2014 | Leight | A61F 11/08 181/135 |
| 2016/0029964 A1* | 2/2016 | LeBoeuf | A61B 5/14551 600/476 |
| 2018/0168465 A1 | 6/2018 | Yamada et al. | |
| 2018/0296166 A1* | 10/2018 | LeBoeuf | A61B 5/0261 |

(Continued)

FOREIGN PATENT DOCUMENTS

| | | |
|---|---|---|
| CN | 108209899 A | 6/2018 |
| JP | 2015-123160 A | 7/2015 |
| JP | 2016128034 A | 7/2016 |

(Continued)

*Primary Examiner* — Tammie K Marlen
*Assistant Examiner* — Maria Catherine Anthony
(74) *Attorney, Agent, or Firm* — Studebaker & Brackett PC (57) ABSTRACT

An electronic device comprises an insertion portion, a sensor, and a controller. The insertion portion is configured to be at least partly inserted in an external ear canal of a user. The sensor is configured to detect a signal relating to an organism of the user, in a state in which at least part of the insertion portion is inserted in the external ear canal of the user. The controller is configured to perform a predetermined process, based on a signal that satisfies a predetermined condition from among the signal relating to the organism of the user detected by the sensor.

21 Claims, 8 Drawing Sheets

(56) References Cited

U.S. PATENT DOCUMENTS

2020/0221961 A1    7/2020  Ishihara et al.
2021/0267464 A1*   9/2021  Hirano .................. A61B 5/741

FOREIGN PATENT DOCUMENTS

| | | | | |
|---|---|---|---|---|
| JP | 2017-225881 | A | 12/2017 | |
| JP | 2018-027184 | A | 2/2018 | |
| JP | 2018161432 | A | 10/2018 | |
| JP | 2019050853 | A | 4/2019 | |
| JP | 2019118524 | A | 7/2019 | |
| KR | 10-2008-0051900 | A | 6/2008 | |
| WO | WO-2016067942 | A1 * | 5/2016 | .............. A61B 5/02 |
| WO | WO-2018013835 | A1 * | 1/2018 | |
| WO | 2018066679 | A1 | 4/2018 | |
| WO | 2018110534 | A1 | 6/2018 | |

* cited by examiner

ELECTRONIC DEVICE, CONTROL METHOD, AND CONTROL PROGRAM

CROSS REFERENCE TO RELATED APPLICATION

This application claims priority to and the benefit of Japanese Patent Application No. 2019-146594 filed on Aug. 8, 2019, the entire disclosure of which is incorporated herein by reference.

TECHNICAL FIELD

The present disclosure relates to an electronic device, a control method, and a control program.

BACKGROUND

Studies to detect the sleep state of a subject by measuring the biological information of the subject have been conventionally promoted. For example, JP 2018-161432 A (PTL 1) proposes a means of detecting non-REM sleep of a subject based on the heart beat of the subject.

CITATION LIST

Patent Literature

PTL 1: JP 2018-161432 A

SUMMARY

An electronic device according to an embodiment comprises an insertion portion, a sensor, and a controller. The insertion portion is configured to be at least partly inserted in an external ear canal of a user. The sensor is configured to detect a signal relating to an organism of the user, in a state in which at least part of the insertion portion is inserted in the external ear canal of the user. The controller is configured to perform a predetermined process, based on a signal that satisfies a predetermined condition from among the signal relating to the organism of the user detected by the sensor.

A method according to an embodiment is a control method of an electronic device that includes: an insertion portion configured to be at least partly inserted in an external ear canal of a user; and a sensor configured to detect a signal relating to an organism of the user, in a state in which at least part of the insertion portion is inserted in the external ear canal of the user. The control method comprises performing a predetermined process, based on a signal that satisfies a predetermined condition from among the signal relating to the organism of the user detected by the sensor.

A program according to an embodiment is a control program of an electronic device that includes: an insertion portion configured to be at least partly inserted in an external ear canal of a user; and a sensor configured to detect a signal relating to an organism of the user, in a state in which at least part of the insertion portion is inserted in the external ear canal of the user.

The control program causes a controller to perform a predetermined process, based on a signal that satisfies a predetermined condition from among the signal relating to the organism of the user detected by the sensor.

DETAILED DESCRIPTION

In the present disclosure, an "electronic device" may be a device driven by power. In the present disclosure, a "user" may be a subject (human or animal) that uses an electronic device according to an embodiment.

Improvement in the accuracy of measuring biological information of a user of an electronic device is useful, for example, for better detection of the sleep state of the user. It could be helpful to provide an electronic device, a control method, and a control program that can improve the accuracy of measuring biological information. According to an embodiment, an electronic device, a control method, and a control program that can improve the accuracy of measuring biological information can be provided. An electronic device according to an embodiment will be described in detail below, with reference to the drawings.

Figure 1:
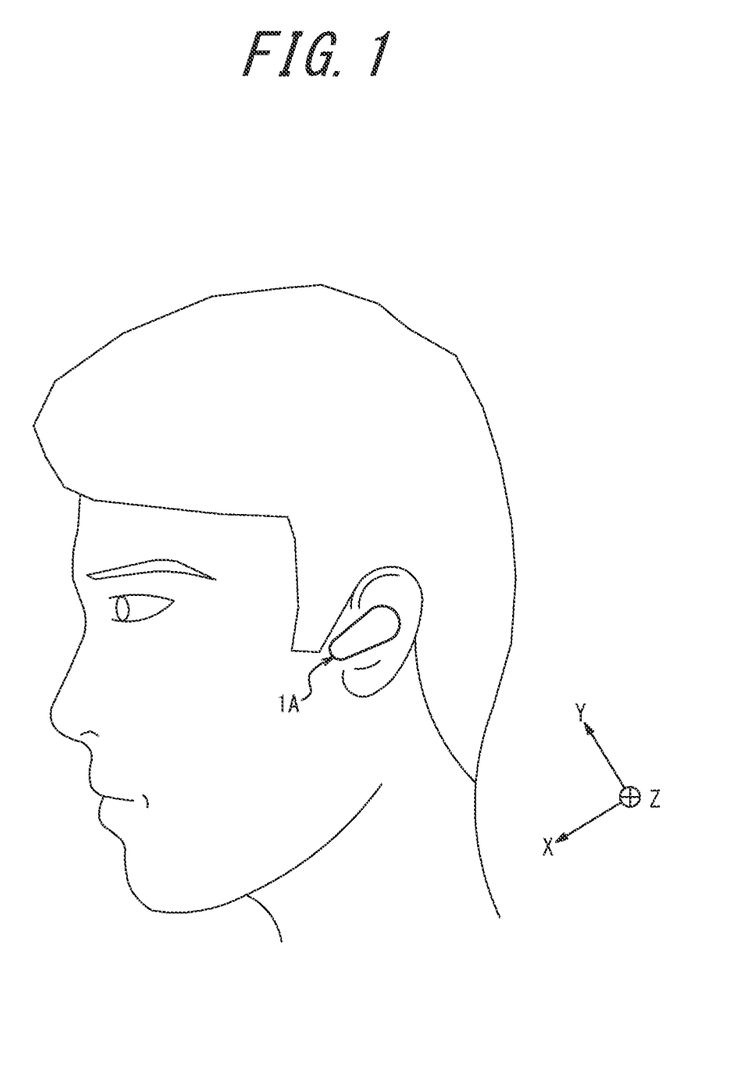
FIG. 1 is a diagram illustrating a state in which an electronic device according to an embodiment is worn by a user.

FIG. 1 is a diagram illustrating a state in which an electronic device according to an embodiment is worn by a user. In detail, FIG. 1 is a diagram illustrating a state in which an electronic device according to an embodiment is worn on or inserted in an ear of a user.

As illustrated in FIG. 1, an electronic device 1A according to an embodiment may be shaped like an earphone or an earplug. As illustrated in FIG. 1, the electronic device 1A according to the embodiment may be configured to be usable in a state of being worn on or inserted in an ear of a user. In this case, the electronic device 1A according to the embodiment may have an earplug function of preventing sound from entering the ear of the user. The electronic device 1A according to the embodiment may detect a signal relating to the organism of the user at the ear of the user in a state of being worn on or inserted in the ear of the user. The electronic device 1A according to the embodiment can perform various predetermined processes based on the signal detected in this way. For example, the electronic device 1A according to the embodiment may measure the blood flow amount of the user based on the detected signal relating to the organism of the user. For example, the electronic device 1A according to the embodiment may output sound that wakes the user from sleep at a timing determined based on the measured blood flow amount of the user.

FIG. 1 illustrates the electronic device 1A worn on or inserted in the left ear of the user. As illustrated in FIG. 1, the electronic device 1A may be worn on or inserted in the left ear of the user. Alternatively, the electronic device 1A may be worn on or inserted in the right ear of the user. Thus, the electronic device 1A according to the embodiment may be configured to be worn on or inserted in only one ear of the user.

Alternatively, two electronic devices 1A according to the embodiment may be worn on or inserted in one user. In this case, the respective two electronic devices 1A may be worn on or inserted in the right and left ears of the user.

An electronic device having a structure bilaterally symmetrical to the electronic device 1A as viewed from the user illustrated in FIG. 1 may be provided as an electronic device 1B according to the embodiment. In this case, for example, the electronic device 1A may be configured to be worn on or inserted in the left ear of the user, and the electronic device 1B may be configured to be worn on or inserted in the right ear of the user. Hereafter, the electronic device 1A is also referred to as "left ear electronic device 1A", and the electronic device 1B is also referred to as "right ear electronic device 1B". In the following description, "A" in the reference signs may be replaced with "B" as appropriate to take the description about the left ear electronic device 1A to be about the right ear electronic device 1B. In the case where the electronic device 1A and the electronic device 1B are not distinguished from each other, they are also simply referred to as "electronic device 1". The right ear electronic device 1B may have an appearance bilaterally symmetrical to the left ear electronic device 1A from the user's viewpoint. The right ear electronic device 1B may have the same functions as the left ear electronic device 1A. The right ear electronic device 1B is omitted in the drawings.

The electronic device 1A illustrated in FIG. 1 has a shape that is elongated in a direction parallel to the X-axis in the drawing. The electronic device 1A according to the embodiment is, however, not limited to the shape illustrated in FIG. 1. The electronic device 1A according to the embodiment may have, for example, a rectangular shape, a square shape, an elliptical shape, or a circular shape. The electronic device 1A according to the embodiment may have any shape based on design and the like. The appearance shape of the electronic device 1A according to the embodiment may be suitable for being worn on or inserted in the ear of the user.

Figure 2:
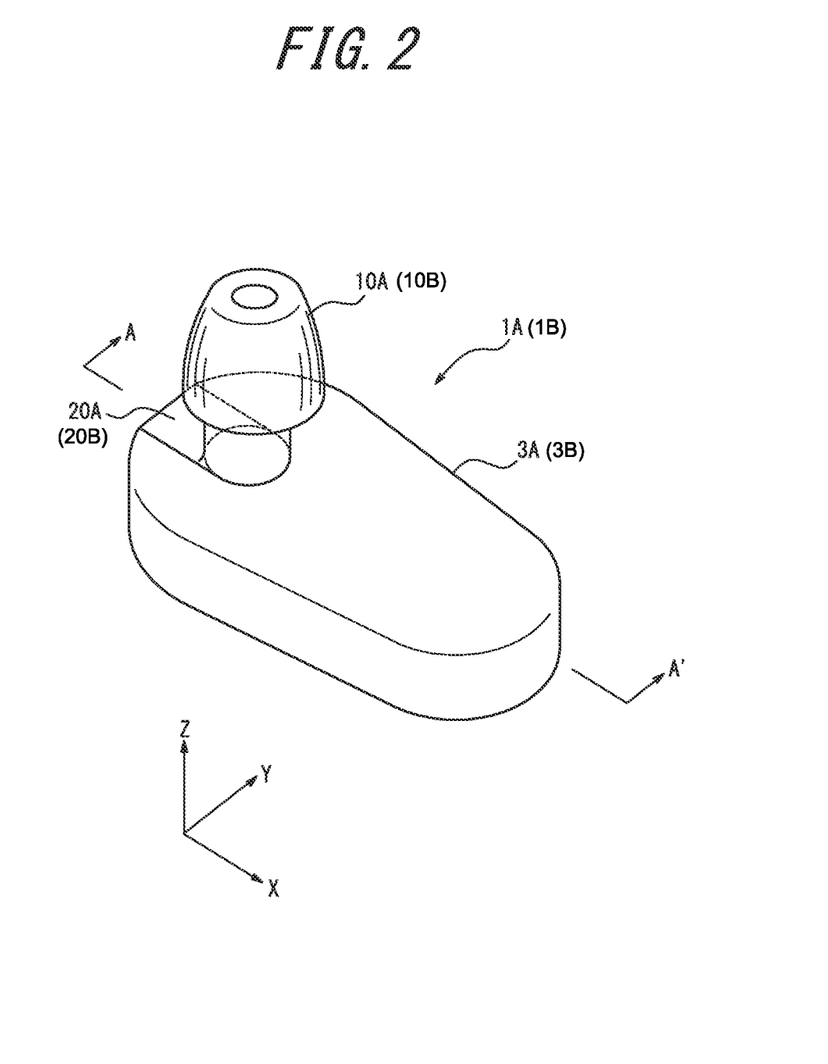
FIG. 2 is an appearance diagram of the electronic device according to the embodiment.

FIG. 2 is an appearance diagram of the electronic device 1A according to the embodiment. FIG. 2 is a diagram illustrating a state in which the electronic device 1 illustrated in FIG. 1 is removed from the ear of the user.

As illustrated in FIG. 2, the electronic device 1A according to the embodiment includes a main body 3A, an insertion portion 10A, and a sensor 20A. The electronic device 1B according to the embodiment may include a main body 3B, an insertion portion 10B, and a sensor 20B. Hereafter, the main body 3A is also referred to as "left ear main body 3A", and the main body 3B is also referred to as "right ear main body 3B". In the case where the main body 3A and the main body 3B are not distinguished from each other, they are also simply referred to as "main body 3". The insertion portion 10A is also referred to as "left ear insertion portion 10A", and the insertion portion 10B is also referred to as "right ear insertion portion 10B". In the case where the insertion portion 10A and the insertion portion 10B are not distinguished from each other, they are also simply referred to as "insertion portion 10". The sensor 20A is also referred to as "left ear sensor 20A", and the sensor 20B is also referred to as "right ear sensor 20B". In the case where the sensor 20A and the sensor 20B are not distinguished from each other, they are also simply referred to as "sensor 20".

The main body 3 may be a housing of the electronic device 1. The main body 3 may be made of any material having strength to function as the housing of the electronic device 1, such as synthetic resin, aluminum, or rubber. The electronic device 1 according to the embodiment may include various components inside the main body 3. The main body 3 may have any shape and size and is not limited to the shape illustrated in FIG. 2 as an example, as mentioned above. In an embodiment, the main body 3 may have a shape and size suitable for being worn on or inserted in the ear of the user.

The insertion portion 10 is a portion inserted in the ear of the user. The ear of the user in which the insertion portion 10 is inserted may be, for example, the external ear canal of the user. In this case, at least part of the insertion portion 10 may be inserted in the external ear canal of the user. Hence, the insertion portion 10 may be made of, for example, a silicon-based material, or a low-resilience material such as an urethane material. The insertion portion 10 may include a removable earpiece that can be changed in size as appropriate so as to be in close contact with the external ear canal of the user. That is, the insertion portion 10 may include a replaceable earpiece. In this case, the earpiece may prevent sound from entering the external ear canal of the user in a state in which at least part of the insertion portion 10 is inserted in the external ear canal of the user. In other words, the electronic device 1 may prevent external sound from entering the external ear canal of the user, as a result of at least part of the insertion portion 10 being inserted in the external ear canal of the user. In such a case, the electronic device 1 including the insertion portion 10 has an effect of an earplug.

Thus, the insertion portion 10 may be at least partly inserted in the external ear canal of the user. That is, at least part of the insertion portion 10 may be inserted in the external ear canal of the user. The insertion portion 10 may include the left ear insertion portion 10A (first insertion portion) that is at least partly inserted in the external ear canal of the left ear of the user, and the right ear insertion portion 10B (second insertion portion) that is at least partly inserted in the external ear canal of the right ear of the user. The insertion portion 10 may further include an earpiece that prevents sound from entering the external ear canal of the user in a state in which at least part of the insertion portion 10 is inserted in the external ear canal of the user.

The sensor 20 detects a signal relating to the organism of the user at the ear of the user. In an embodiment, the sensor 20 may detect the signal relating to the organism of the user in a state in which at least part of the insertion portion 10 is inserted in the external ear canal of the user as described above. In an embodiment, the sensor 20 may be a laser sensor as described later. The sensor 20 is, however, not limited to a laser sensor, and may be an LED sensor or the like.

Thus, the sensor 20 detects the signal relating to the organism of the user at the ear of the user, in a state in which at least part of the insertion portion 10 is inserted in the external ear canal of the user. In an embodiment, the sensor 20 may include the left ear sensor 20A (first sensor). In this case, the left ear sensor 20A may measure the information relating to the organism of the user at the left ear of the user in a state in which at least part of the left ear insertion portion 10A is inserted in the external ear canal of the left ear of the user. In an embodiment, the sensor 20 may include the right ear sensor 20B (second sensor). In this case, the right ear sensor 20B may measure the information relating to the organism of the user at the right ear of the user in a state in which at least part of the right ear insertion portion 10B is inserted in the external ear canal of the right ear of the user.

Figure 3:
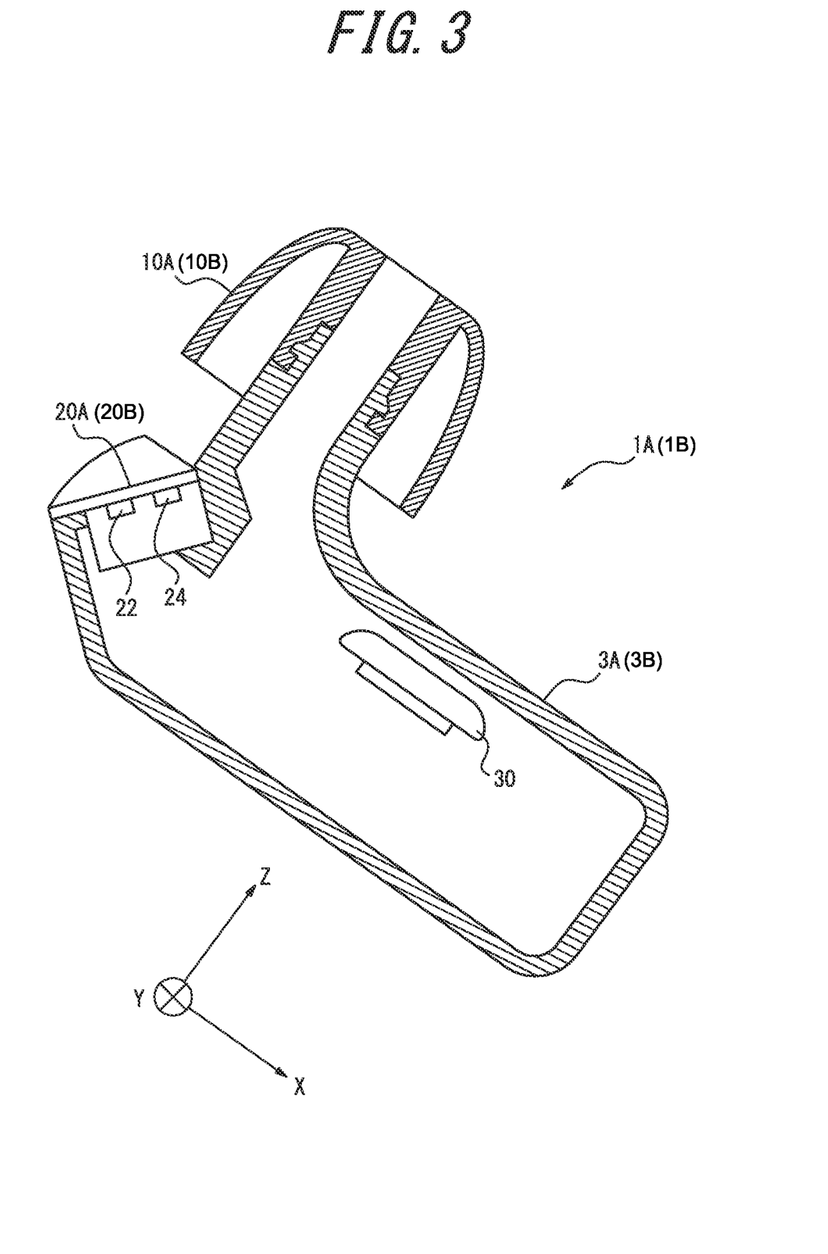
FIG. 3 is a sectional diagram of the electronic device according to the embodiment.

FIG. 3 is a sectional diagram of the electronic device according to the embodiment. FIG. 3 is a sectional diagram along line A-A' of the electronic device 1A illustrated in FIG. 2.

As illustrated in FIG. 3, the electronic device 1A according to the embodiment includes the main body 3A, the insertion portion 10A, and the sensor 20A. FIG. 3 illustrates an example in which the insertion portion 10A includes a removable earpiece.

As illustrated in FIG. 3, in the electronic device 1A according to the embodiment, the sensor 20A may include an optical emitter 22 and an optical detector 24. In an embodiment, the sensor 20A may include, for example, a laser Doppler velocimeter. The laser Doppler velocimeter itself is known, and accordingly its detailed description is omitted. The sensor 20A including the laser Doppler velocimeter in the electronic device 1A according to the embodiment can measure, for example, the blood flow amount at the ear of the user.

The sensor 20A illustrated in FIGS. 2 and 3 is located at a position where the signal relating to the organism of the user can be detected at around the cavity of the ear concha of the left ear of the user. The position of the sensor 20A illustrated in FIGS. 2 and 3 is an example. In the electronic device 1A according to the embodiment, the sensor 20A may be located at any of various positions where the signal relating to the organism of the user can be detected at the ear of the user in a state in which at least part of the insertion portion 10 is inserted in the external ear canal of the user.

As illustrated in FIG. 3, the electronic device 1A according to the embodiment may include a driver unit 30 inside the main body 3. The driver unit 30 may be a device capable of outputting sound, such as a device used in a typical earphone or the like. As illustrated in FIG. 3, the driver unit 30 can output sound from the insertion portion 10 toward the external ear canal of the user by causing air vibration. The driver unit itself is known, and accordingly its detailed description is omitted.

The driver unit 30 illustrated in FIG. 3 is located near the insertion portion 10A that is inserted in the external ear canal of the user, in the main body 3A of the electronic device 1A. The position of the driver unit 30 illustrated in FIG. 3 is an example. The driver unit 30 may be located at any position where sound can be output from the insertion portion 10 to the inside of the external ear canal of the user, in the main body 3A of the electronic device 1A according to the embodiment.

Figure 4:
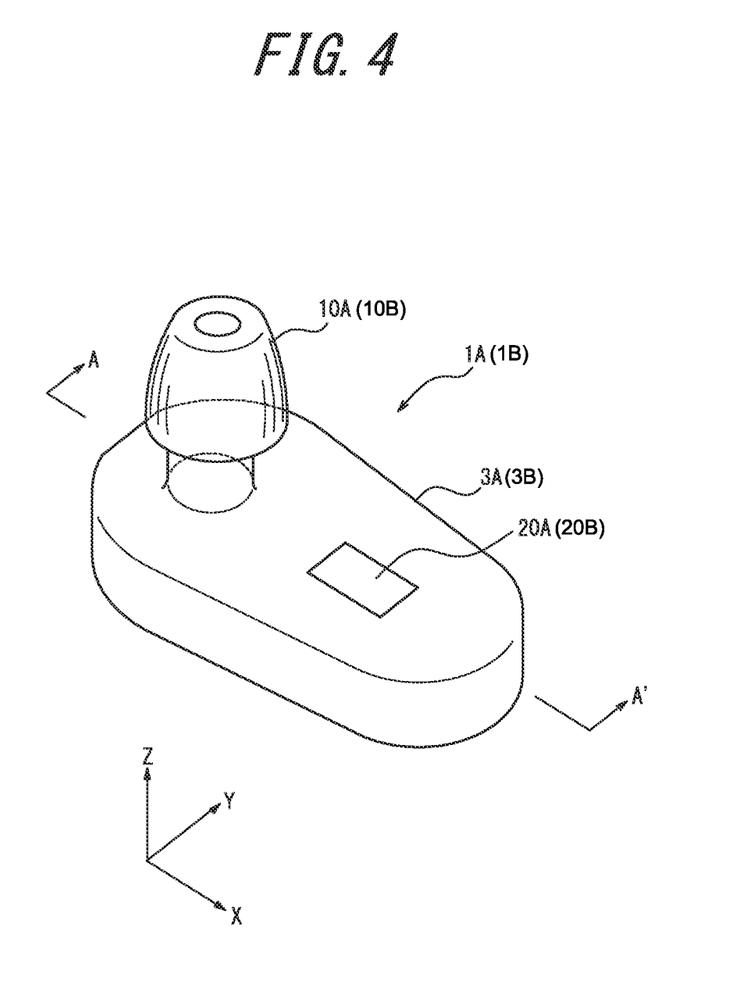
FIG. 4 is an appearance diagram of the electronic device according to the embodiment.
Figure 5:
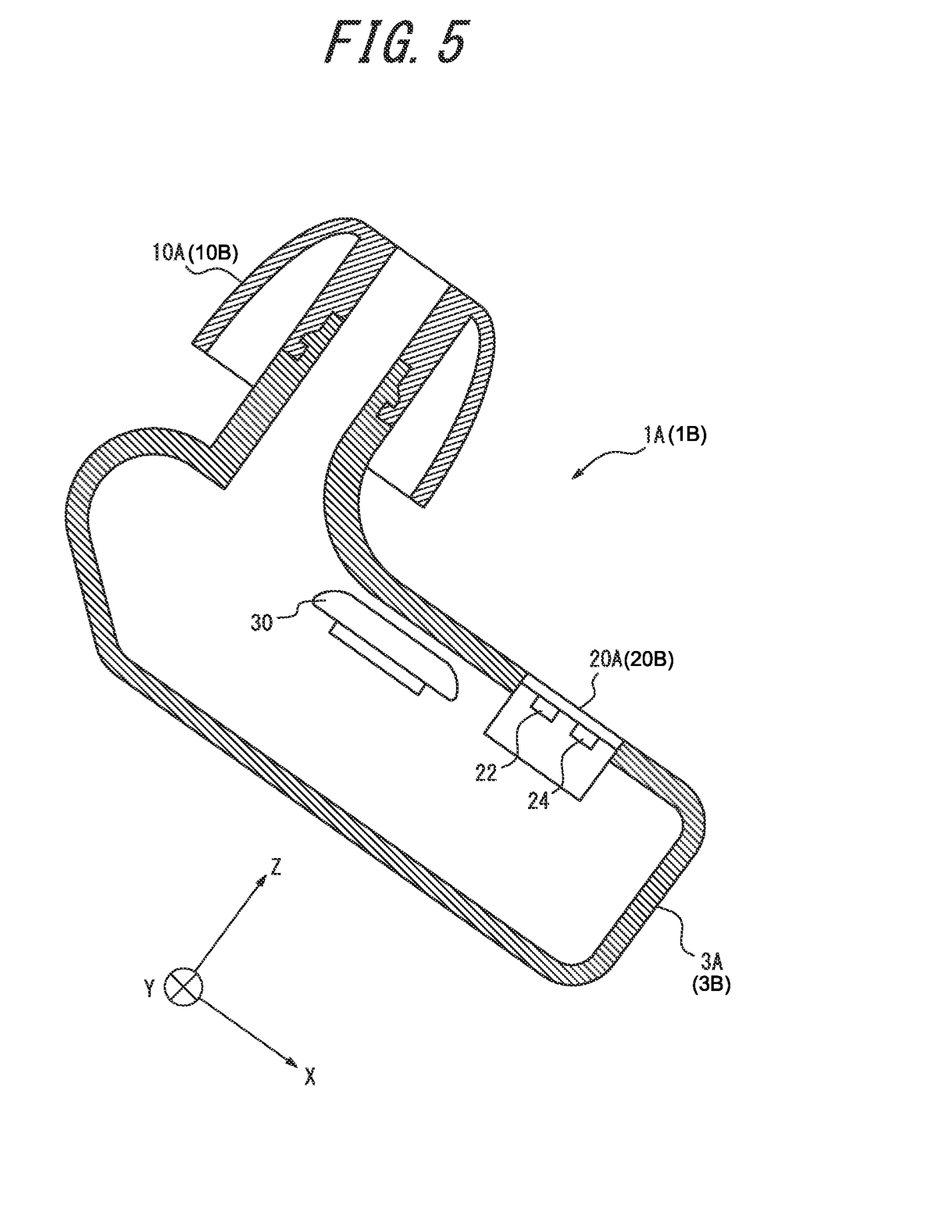
FIG. 5 is a sectional diagram of the electronic device according to the embodiment.

In the present disclosure, the position of the sensor 20 is not limited to the example illustrated in FIGS. 2 and 3, and may be any appropriate position. For example, at least one of the left ear sensor 20A and the right ear sensor 20B may be located at a center part of the main body 3, as illustrated in FIG. 4. The sensor 20 may then acquire the biological information from the ear concha of the user. In this case, the sensor 20A including the optical emitter 22 and the optical detector 24 is directed toward the ear concha of the user, as illustrated in FIG. 5.

Figure 6:
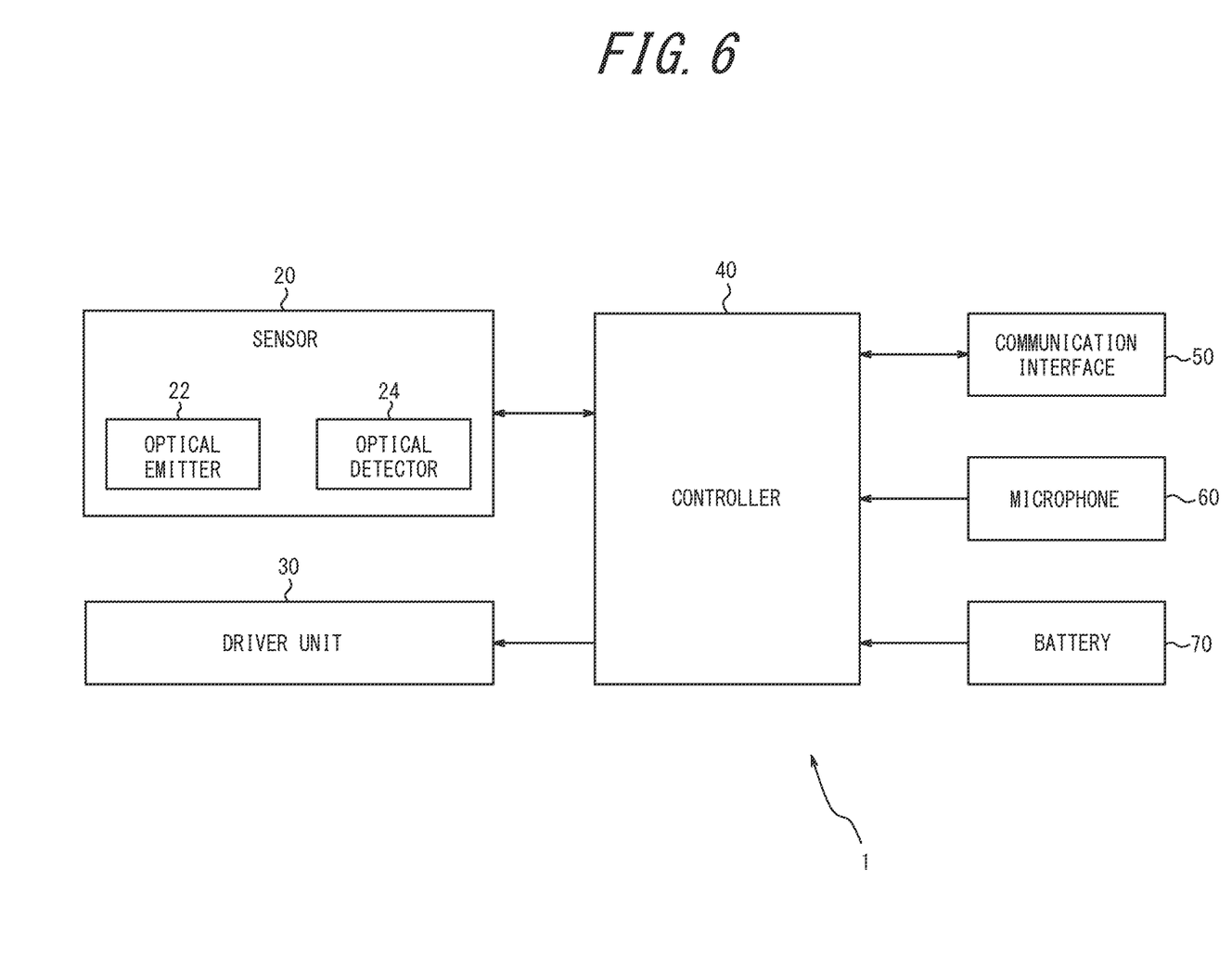
FIG. 6 is a functional block diagram illustrating a schematic structure of the electronic device according to the embodiment.

FIG. 6 is a functional block diagram schematically illustrating a structure of the electronic device 1 according to the embodiment. FIG. 6 illustrates elements constituting the electronic device 1 according to the embodiment. The electronic device 1 according to the embodiment may not necessarily include all of the functional parts illustrated in FIG. 6. The electronic device 1 according to the embodiment may include one or more functional parts other than those illustrated in FIG. 6.

The electronic device 1 illustrated in FIG. 6 includes the sensor 20, the driver unit 30, a controller 40, a communication interface 50, a microphone 60, and a battery 70.

The sensor 20 may include, for example, the optical emitter 22 and the optical detector 24, as illustrated in FIG. 3. The sensor 20 detects the signal relating to the organism of the user at the ear of the user, in a state in which at least part of the insertion portion 10 is inserted in the external ear canal of the user. The sensor 20 may include, for example, a laser Doppler velocimeter or the like, as mentioned above. The sensor 20A including the laser Doppler velocimeter can measure, for example, the blood flow amount at the ear of the user. The sensor 20 may detect the signal relating to the organism of the user based on control by the controller 40. For example, the signal detected by the sensor 20 may be supplied to the controller 40. In more detail, the controller 40 may control the light emission of the optical emitter 22 in the sensor 20. The signal based on the light received by the optical detector 24 in the sensor 20 may be supplied to the controller 40.

The driver unit 30 can make various notifications to the user by outputting various types of sound. For example, the driver unit 30 may output sound by supplying an electric signal to a diaphragm or the like to cause air vibration. The driver unit 30 may include any speaker. The driver unit 30 may output a signal supplied from the controller 40, as sound.

In the electronic device 1A according to the embodiment, for example, the driver unit 30 may output predetermined environmental sound or the like based on control by the controller 40, in order to promote the sleep of the user. In the electronic device 1A according to the embodiment, for example, the driver unit 30 may output predetermined sound or the like (e.g. alarm sound that gradually increases in volume) based on control by the controller 40, in order to wake the user from sleep. In this case, the controller 40 may control the driver unit 30 to output predetermined sound or the like at a timing set by the user, for example.

In an embodiment, information of the sound output from the driver unit 30 may be stored in memory included in the controller 40 or other memory. The information of the sound stored in the memory may be an audio file in any format such as an MP3 (MPEG-1 Audio Layer-3) file or a WAV file.

Thus, in the electronic device 1A according to the embodiment, the controller 40 may control the driver unit 30 to output predetermined sound at a predetermined timing set beforehand.

The controller 40 controls and/or manages the whole electronic device 1, such as the functional parts included in the electronic device 1. The controller 40 may include at least one processor such as a central processing unit (CPU), to provide control and processing capacity for achieving various functions. The controller 40 may be implemented by one processor, by several processors, or by respective separate processors. Each processor may be implemented as a single integrated circuit (IC). Each processor may be implemented as a plurality of integrated circuits and/or discrete circuits communicably connected to one another. Each processor may be implemented based on any of other various known techniques.

In an embodiment, the controller 40 may be implemented, for example, by a CPU and a program executed by the CPU. The program executed by the controller 40, results of processes performed by the controller 40, and the like may be, for example, stored in memory. The controller 40 may include memory necessary for the operation of the controller

40 as appropriate. The operation of the controller 40 in the electronic device 1 according to the embodiment will be described in detail later.

The memory may store the program executed by the controller 40, the results of the processes performed by the controller 40, and the like. The memory may function as work memory of the controller 40. For example, the memory may be semiconductor memory. The memory is, however, not limited to such, and may be any storage device. For example, the memory may be a storage medium such as a memory card inserted in the electronic device 1 according to the embodiment. The memory may be internal memory of the CPU used as the controller 40 as mentioned above, or may be connected to the controller 40 as a separate unit.

The communication interface 50 is an interface for performing wired or wireless communication. The communication interface 50 in the embodiment supports a wireless communication standard. The wireless communication standard is, for example, a communication standard relating to cellular phones such as 2G, 3G, 4G, and 5G. Examples of the communication standard of cellular phones include Long Term Evolution (LTE), Wideband Code Division Multiple Access (W-CDMA), CDMA 2000, Personal Digital Cellular (PDC), Global System for Mobile Communications (GSM® (GSM is a registered trademark in Japan, other countries, or both)), and Personal Handy-phone System (PHS). Examples of the wireless communication standards further include Worldwide Interoperability for Microwave Access (WiMAX), IEEE 802.11, Wi-Fi, Bluetooth® (Bluetooth is a registered trademark in Japan, other countries, or both), Infrared Data Association (IrDA), and Near Field Communication (NFC). The communication interface 50 can support one or more of these communication standards.

Various information transmitted and received by the communication interface 50 may be stored, for example, in the memory included in the controller 40. For example, the communication interface 50 may include an antenna for transmitting and receiving electric waves, an appropriate RF portion, and the like. The communication interface 50 can be implemented by a known technique for performing wireless communication, and accordingly detailed description of its hardware structure is omitted.

The communication interface 50 may transmit, for example, the signal relating to the organism of the user detected by the sensor 20 to an external device (another electronic device) such as a smartphone or a server by wireless communication, based on control by the controller 40. For example, the information transmitted from the communication interface 50 to the external device may be supplied from the controller 40. The communication interface 50 may receive information transmitted from an external device (another electronic device) such as a smartphone or a server by wireless communication. For example, the information received by the communication interface 50 from the external device may be supplied to the controller 40.

In the case where the electronic device 1 according to the embodiment includes the left ear electronic device 1A and the right ear electronic device 1B, the left ear electronic device 1A and the right ear electronic device 1B may each include the communication interface 50. In this case, the left ear electronic device 1A and the right ear electronic device 1B may communicate with each other. In the case where the left ear electronic device 1A and the right ear electronic device 1B are wiredly connected by a cable or the like in the electronic device 1 according to the embodiment, the communication interface 50 in each of the left ear electronic device 1A and the right ear electronic device 1B may be, for example, an interface or a connector connecting the cable.

Thus, the electronic device 1 according to the embodiment may include the communication interface 50 that transmits, to another electronic device, the signal relating to the organism of the user detected by the sensor 20. In an embodiment, in the case where the electronic device 1 is used stand-alone without cooperation with another electronic device and the like, the electronic device 1 need not include the communication interface 50 that provides wireless communication function.

The microphone 60 detects sound around the electronic device 1 (e.g. sound entering the external ear canal of the user), including human voice. The microphone 60 may convert sound detected by a diaphragm or the like as air vibration, into an electric signal. Although the microphone 60 is not illustrated in FIGS. 1 to 3, the electronic device 1 according to the embodiment may include the microphone 60 at any position where sound around the electronic device 1 or sound entering the external ear canal of the user is detectable.

In an embodiment, the controller 40 may generate sound opposite in phase to sound detected by the microphone 60 and output the generated sound from the driver unit 30 (active noise canceling). Thus, in the electronic device 1 according to the embodiment, the controller 40 may control the driver unit 30 to output sound opposite in phase to sound entering the external ear canal of the user. The electronic device 1 according to the embodiment prevents external noise and the like from entering the ear of the user. Therefore, for example by inserting the electronic device 1 in both ears, the user can be put in a quiet environment. Such an environment allows the user to sleep comfortably.

In an embodiment, in the case where the electronic device 1 does not have active noise canceling function, the electronic device 1 need not include the microphone 60.

The battery 70 may supply power to each component of the electronic device 1. The battery 70 may include a rechargeable secondary battery. Examples of the secondary battery include a lithium-ion battery, a nickel-cadmium battery, and a nickel-hydrogen battery. The battery 70 is not limited to a secondary battery, and may include an unrechargeable primary battery. Examples of the primary battery include an alkaline battery and a manganese battery. In an embodiment, in the case where the electronic device 1 is supplied with power from outside, the electronic device 1 need not include the battery 70.

In the case where the electronic device 1 according to the embodiment includes the left ear electronic device 1A and the right ear electronic device 1B, both the left ear electronic device 1A and the right ear electronic device 1B may not necessarily include all of the functional parts illustrated in FIG. 6. For example, in the case where the left ear electronic device 1A and the right ear electronic device 1B are wiredly connected to each other, the controller 40, the communication interface 50, and/or the battery 70 may be included in at least one of the left ear electronic device 1A and the right ear electronic device 1B.

Of the functional parts illustrated in FIG. 6, the controller 40, the communication interface 50, the microphone 60, and the battery 70 are not illustrated in FIG. 3. These functional parts may be located, for example, at any positions in the main body 3A illustrated in FIG. 3.

The operation of the electronic device 1 according to the embodiment will be described below.

As described above, the electronic device 1 according to the embodiment can prevent external sound such as environmental sound from entering the external ear canal of the user, as a result of being worn on or inserted in the ear of the user. Hence, by wearing or inserting the electronic device 1 according to the embodiment on or in the ear, the user can be put in a quiet environment suitable for sleep. The electronic device 1 according to the embodiment can thus detect, by the sensor 20, the signal relating to the organism of the user during sleep of the user.

If the posture of the user changes as a result of, for example, the user turning over in bed while the electronic device 1 according to the embodiment is detecting the signal relating to the organism of the user during sleep of the user, appropriate detection by the sensor 20 may be unable to be continued.

For example, suppose the user having the electronic device 1A inserted in the left ear as illustrated in FIG. 1 lies down and starts sleeping. If the user turns over in sleep and the left side of the head of the user is placed on the floor side, the left side of the head is compressed by the pillow, the bedclothes, or the like. In this case, the electronic device 1A worn on or inserted in the left ear of the user is pressed to, for example, the ear concha of the left ear of the user. This can cause a change in the intensity of light emitted from the optical emitter 22 and/or light received by the optical detector 24. Therefore, even though the sensor 20 has hitherto appropriately detected the signal relating to the organism of the user, such appropriate detection is likely to be no longer maintained.

The same applies to the case where the user having the electronic device 1B inserted in the right ear lies down and starts sleeping. If the user turns over in sleep and the right side of the head of the user is placed on the floor side, the right side of the head is compressed by the pillow, the bedclothes, or the like, and the electronic device 1B worn on or inserted in the right ear of the user is pressed to, for example, the ear concha of the right ear of the user. In this case, too, even though the sensor 20 has hitherto appropriately detected the signal relating to the organism of the user, such appropriate detection is likely to be no longer maintained.

Accordingly, for example, the controller 40 in the electronic device 1 may perform a process based on the signal detected by the sensor 20 only in the case where the controller 40 determines that the signal is appropriately detected by the sensor 20. That is, the controller 40 may subject only the signal appropriately detected by the sensor 20 to a predetermined process. In the case where the controller 40 determines that the signal is not appropriately detected by the sensor 20, the controller 40 may not perform the process based on the signal detected by the sensor 20. That is, the controller 40 may not subject the signal not appropriately detected by the sensor 20 to the predetermined process.

In the case where the electronic device 1 according to the embodiment includes the left ear electronic device 1A and the right ear electronic device 1B, there is a possibility that, even when appropriate detection by the sensor 20 in one electronic device 1 cannot be continued, appropriate detection by the sensor 20 in the other electronic device 1 can be maintained. For example, if the user turns over in sleep and the left side of the head is placed on the floor side, the left ear electronic device 1A is pressed to, for example, the ear concha of the left ear of the user, which may make it impossible to appropriately detect the signal relating to the organism of the user. Even in such a case, since the right ear electronic device 1B is not pressed to, for example, the ear concha of the right ear of the user, the signal relating to the organism of the user can be appropriately detected.

In this case, a process based on the signal detected by the right ear sensor 20B in the right ear electronic device 1B with which the signal relating to the organism of the user is appropriately detected may be performed. That is, the controller 40 may subject, to the predetermined process, only the signal detected by the right ear sensor 20B in the right ear electronic device 1B with which the signal relating to the organism of the user is appropriately detected, from among the left ear electronic device 1A and the right ear electronic device 1B. Meanwhile, a process based on the signal detected by the left ear sensor 20A in the left ear electronic device 1A with which the signal relating to the organism of the user is not appropriately detected may not be performed. That is, the controller 40 may not subject, to the predetermined process, the signal detected by the left ear sensor 20A in the left ear electronic device 1A with which the signal relating to the organism of the user is not appropriately detected, from among the left ear electronic device 1A and the right ear electronic device 1B.

The predetermined process herein may be, for example, a process of measuring the blood flow amount of the user based on the signal relating to the organism of the user. The predetermined process is not limited to a process of measuring the blood flow amount of the user, and may be any process based on the signal relating to the organism of the user.

Figure 7:
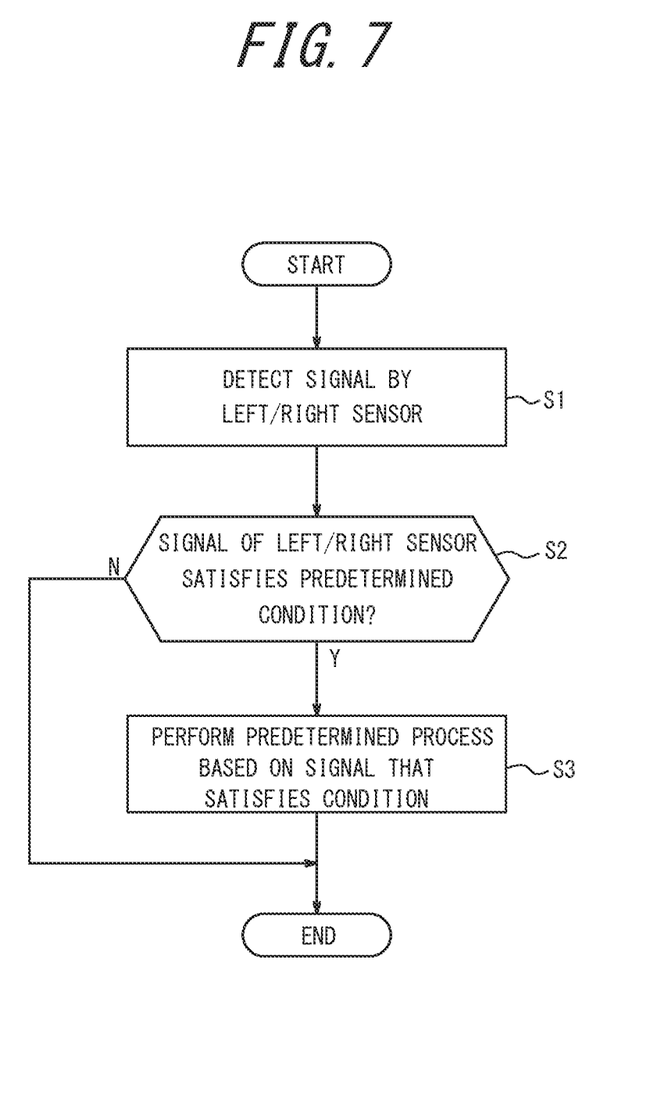
FIG. 7 is a flowchart illustrating an example of operation of the electronic device according to the embodiment.

FIG. 7 is a flowchart illustrating operation of the electronic device 1 according to the embodiment.

The operation illustrated in FIG. 7 may start, for example, when the detection of the signal relating to the organism of the user starts in a state in which the user has the electronic device 1 worn on or inserted in the ear. FIG. 7 illustrates an example in which the electronic device 1 according to the embodiment includes the left ear electronic device 1A and the right ear electronic device 1B. In the case where the electronic device 1 according to the embodiment includes only one of the left ear electronic device 1A and the right ear electronic device 1B, too, operation may be performed in accordance with the procedure in FIG. 7.

When the operation illustrated in FIG. 7 starts, the controller 40 controls both the left ear sensor 20A and the right ear sensor 20B to detect the signal relating to the organism of the user (step S1).

Once the left ear sensor 20A and the right ear sensor 20B have started the detection of the signal relating to the organism of the user in step S1, the controller 40 determines whether the detected signal satisfies a predetermined condition (step S2).

The predetermined condition used for the determination in step S2 may be, for example, the intensity of the detected signal. For example, the predetermined condition in step S2 may be the ratio of the quantity of light received by the optical detector 24 to the quantity of light emitted by the optical emitter 22 in the sensor 20. In step S2, for example, the controller 40 may determine whether the detected signal satisfies the predetermined condition based on the DC value of the intensity of the signal detected by the sensor 20 (i.e. the intensity of light received by the optical detector 24).

The predetermined condition in step S2 may be set in any of various forms.

For example, the predetermined condition in step S2 may be a threshold set based on the signal detected by the sensor 20 when the user wears the electronic device 1 onto the ear or inserts the electronic device 1 into the ear. To wear the electronic device 1 onto the ear or insert the electronic device 1 into the ear, the user pushes the electronic device 1 into the ear, so that the electronic device 1 is pressed to the ear of the user harder than in a normal wearing or insertion state in which the electronic device 1 is already worn on or inserted in the ear. Hence, the threshold as the predetermined condition may be set based on the signal detected by the sensor 20 when the electronic device 1 is pressed to the ear of the user harder than in the normal wearing or insertion state. In this case, for example, the threshold as the predetermined condition may be set based on the lower limit (lower limit value) of the DC signal detected by the sensor 20 when the user wears the electronic device 1 onto the ear or inserts the electronic device 1 into the ear. For example, the controller 40 may determine that the predetermined condition is not satisfied in step S2, in the case where the signal detected by the sensor 20 is less than the lower limit value of the DC value.

For example, the predetermined condition in step S2 may be a threshold set based on the signal detected by the sensor 20 up to the present and/or the signal detected by the sensor 20 in the past. In the case where the user routinely detects the signal relating to the organism of the user by the electronic device 1, for example, the controller 40 can obtain the signal relating to the organism of the respective user in normal time. Hence, the predetermined condition in step S2 may be a range set based on a record (or history) of the signal relating to the organism of the user in normal time. For example, the controller 40 may determine that the predetermined condition is satisfied in step S2, in the case where the intensity of the detected signal is within the set range. The controller 40 may determine that the predetermined condition is not satisfied in step S2, in the case where the intensity of the detected signal is not within the set range. In this case, the predetermined condition in step S2 may be a threshold or a range set based on the average DC value obtained from the record (or history) of the signal relating to the organism of the user in normal time. For example, the controller 40 may determine that the predetermined condition is not satisfied in step S2, in the case where the signal detected by the sensor 20 is less than 50% of the average DC value.

In the case where the detected signal satisfies the predetermined condition in step S2 (step S2: Yes), the controller 40 performs the predetermined process based on the signal determined to satisfy the predetermined condition (step S3), and then ends the procedure illustrated in FIG. 7. The predetermined process in step S3 may be any process based on the signal relating to the organism of the user, as mentioned above. In the case where the detected signal does not satisfy the predetermined condition in step S2 (step S2: No), the controller 40 ends the procedure illustrated in FIG. 7 without performing the process in step S3. That is, in the operation illustrated in FIG. 7, only a signal of an appropriate detection value by the sensor 20 from among the left ear electronic device 1A and the right ear electronic device 1B is used for the process, and a signal that is not appropriate is not used for the process.

Thus, in the electronic device 1 according to the embodiment, the controller 40 may perform the predetermined process based on the signal that satisfies the predetermined condition from among the signal relating to the organism of the user detected by the sensor 20. In an embodiment, the controller 40 may perform the predetermined process based on the signal that satisfies the predetermined condition from among the signal relating to the organism of the user detected by the left ear sensor 20A and the signal relating to the organism of the user detected by the right ear sensor 20B.

In this case, the controller 40 may perform the predetermined process based on a signal having at least a predetermined intensity from among the signal relating to the organism of the user detected by the sensor 20. The controller 40 may perform the predetermined process based on a signal having an intensity within a predetermined range from among the signal relating to the organism of the user detected by the sensor 20.

With the electronic device 1 according to the embodiment, a signal appropriately detected by the sensor 20 can be subjected to the process, without subjecting a signal not appropriately detected by the sensor 20 to the process. The electronic device 1 according to the embodiment can therefore improve the accuracy of measuring the biological information of the user. With improvement in the accuracy of measuring the biological information of the user, the electronic device 1 according to the embodiment can be expected to improve, for example, the accuracy of measuring the blood flow amount of the user. Based on the accurately measured blood flow amount of the user, the electronic device 1 according to the embodiment can detect, for example, the sleep state of the user more favorably.

Figure 8:
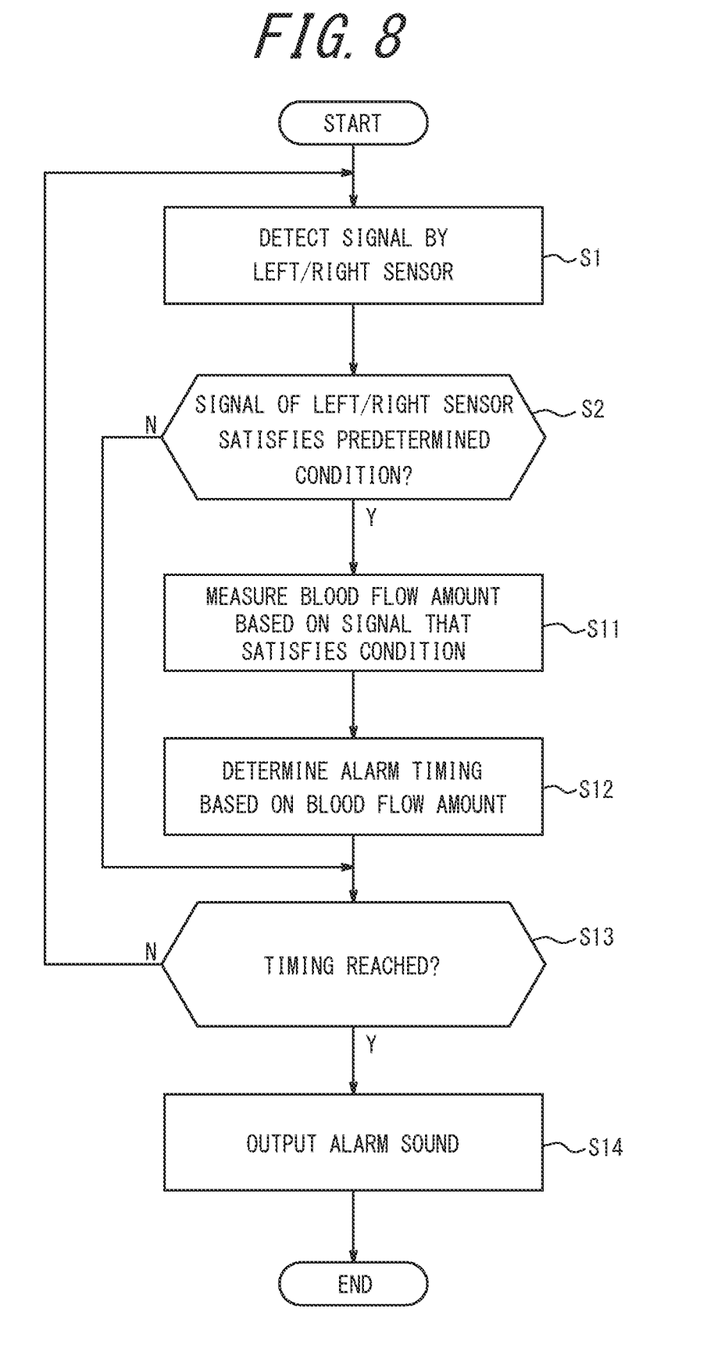
FIG. 8 is a flowchart illustrating an example of operation of the electronic device according to the embodiment.

FIG. 8 is a flowchart illustrating another operation of the electronic device 1 according to the embodiment.

The operation illustrated in FIG. 8 results from adding more functions to the foregoing operation illustrated in FIG. 7. Regarding FIG. 8, the same description as in FIG. 7 is simplified or omitted as appropriate.

When the operation illustrated in FIG. 8 starts, the controller 40 performs the processes in steps S1 and S2, as in FIG. 7.

In the case where the detected signal satisfies the predetermined condition in step S2 in FIG. 8 (step S2: Yes), the controller 40 performs the processes in steps S11 and S12 in FIG. 8, instead of step S3 in FIG. 7.

The process in step S11 in FIG. 8 is roughly the same as the process in step S3 in FIG. 7. In step S11, the controller 40 measures the blood flow amount of the user as the predetermined process, based on the signal determined to satisfy the predetermined condition (step S11).

After the blood flow amount of the user is measured in step S11, for example, the controller 40 determines a suitable timing (e.g. a time of day) of waking the user from sleep based on the measured blood flow amount (step S12). Various research papers have been published on the relationship between the blood flow amount and the depth of sleep of humans. With reference to such research, the controller 40 may determine an appropriate timing so that the sleep of the user will not be excessively deep or excessively light, based on the blood flow amount of the user. After determining the timing of waking the user from sleep in step S12, the controller 40 performs the process in step S13.

In the case where the detected signal does not satisfy the predetermined condition in step S2 (step S2: No), the controller 40 may perform the process in step S13, without performing the processes in steps S11 and S12.

In step S13, the controller 40 determines whether the determined timing has been reached. In the case where the timing has not been reached in step S13, the controller 40 returns to step S1 and continues the procedure. In the case where the timing has been reached in step S13, the controller 40 outputs predetermined sound such as alarm sound from the driver unit (step S14). In the case where the timing has been reached in step S13, the controller 40 may output at least one of sound, vibration, and light to wake the user (step S14).

In the operation illustrated in FIG. 8, even after the timing of waking the user from sleep is determined in step S12, the timing can be redetermined (i.e. changed) based on the subsequently measured biological information of the user. Alternatively, the operation illustrated in FIG. 8 may be modified so that, once the timing of waking the user from sleep has been determined, the timing will not be changed until the timing is reached. In detail, in the case where the timing has not been reached in step S13, the controller 40 may wait the timing to be reached in step S13, instead of returning to step S1.

Thus, in the electronic device 1 according to the embodiment, the controller 40 may measure the blood flow amount of the user based on the signal that satisfies the predetermined condition from among the signal relating to the organism of the user detected by the sensor 20. Moreover, in the electronic device 1 according to the embodiment, the controller 40 may control the driver unit 30 to output sound at a timing determined based on the blood flow amount of the user.

The electronic device 1 according to the embodiment can wake the user from sleep at an appropriate timing, while creating an easy-to-sleep environment for the user. The electronic device 1 according to the embodiment can thus function as a good-sleep device with an alarm.

Although the embodiments according to the present disclosure have been described by way of the drawings and examples, various changes or modifications may be easily made by those of ordinary skill in the art based on the present disclosure. Such various changes or modifications are therefore included in the scope of the present disclosure. For example, the functions included in the components, steps, etc. may be rearranged without logical inconsistency, and a plurality of components, steps, etc. may be combined into one component, step, etc. and a component, step, etc. may be divided into a plurality of components, steps, etc. Although devices have been mainly described in the embodiments according to the present disclosure, the embodiments according to the present disclosure can also be implemented as methods including the steps executed by the components included in the devices. The embodiments according to the present disclosure can also be implemented as methods or programs executed by processors included in the devices or storage media storing such programs, which are also included in the scope of the present disclosure.

The foregoing embodiments are not limited to implementation as the electronic device 1. For example, the foregoing embodiments may be implemented as a control method of a device such as the electronic device 1. For example, the foregoing embodiments may be implemented as a control program of a device such as the electronic device 1. The control program is not limited to be executed on the electronic device 1, and may be executed on another electronic device, such as a smartphone, that cooperates with the electronic device 1.

The electronic device 1 according to the foregoing embodiments is described as a device that prevents sound from entering the ear of the user. Alternatively, for example, the insertion portion 10 may have a through hole to allow external sound to enter the external ear canal of the user.

REFERENCE SIGNS LIST 1 electronic device
1A left ear electronic device
1B right ear electronic device
3 main body
3A left ear main body
3B right ear main body
10 insertion portion
10A left ear insertion portion
10B right ear insertion portion
20 sensor
20A left ear sensor
20B right ear sensor
22 optical emitter
24 optical detector
30 driver unit
40 controller
50 communication interface
60 microphone
70 battery

The invention claimed is:

1. An electronic device comprising:
an insertion portion configured to be at least partly inserted in an external ear canal of a user;
a sensor configured to detect a signal relating to an organism of the user, in a state in which at least part of the insertion portion is inserted in the external ear canal of the user;
a driver unit configured to output sound from the insertion portion; and
a controller configured to perform a predetermined process, based on a signal relating to the organism of the user detected by the sensor that satisfies a predetermined condition,
wherein the controller is configured to measure a blood flow rate of the user, based on the signal relating to the organism of the user detected by the sensor that satisfies the predetermined condition,
the controller is configured to determine a timing to output the sound based on a relationship between the measured blood flow rate of the user and a depth of sleep of humans, and
the controller is configured to control the driver unit to output the sound at the determined timing.

2. The electronic device according to claim 1, wherein the insertion portion includes: a first insertion portion configured to be at least partly inserted in an external ear canal of a left ear of the user; and a second insertion portion configured to be at least partly inserted in an external ear canal of a right ear of the user, and
the sensor includes: a first sensor configured to measure information relating to the organism of the user in a state in which at least part of the first insertion portion is inserted in the external ear canal of the left ear of the user; and a second sensor configured to measure information relating to the organism of the user in a state in which at least part of the second insertion portion is inserted in the external ear canal of the right ear of the user.

3. The electronic device according to claim 2, wherein the controller is configured to perform the predetermined process, based on the signal relating to the organism of the user detected by the first sensor and the signal relating to the organism of the user detected by the second sensor that satisfy the predetermined condition.

4. The electronic device according to claim 1, wherein the sensor includes an optical emitter and an optical detector.

5. The electronic device according to claim 1, wherein the sensor includes a laser Doppler velocimeter.

6. The electronic device according to claim 1, wherein the insertion portion includes an earpiece configured to prevent sound from entering the external ear canal of the user from outside the electronic device in the state in which the at least part of the insertion portion is inserted in the external ear canal of the user.

7. The electronic device according to claim 1, wherein the controller is configured to control the driver unit to output predetermined sound at a predetermined timing set beforehand.

8. The electronic device according to claim 1, wherein the controller is configured to control the driver unit to output sound opposite in phase to sound entering the external ear canal of the user.

9. The electronic device according to claim 1, wherein the controller is configured to perform the predetermined process, based on a signal relating to the organism of the user detected by the sensor and having at least a predetermined intensity.

10. The electronic device according to claim 1, wherein the controller is configured to perform the predetermined process, based on a signal relating to the organism of the user detected by the sensor and having an intensity within a predetermined range.

11. The electronic device according to claim 1, comprising
a communication interface configured to transmit the signal relating to the organism of the user detected by the sensor, to an other electronic device.

12. The electronic device according to claim 1, wherein the sensor is configured to detect the signal relating to the organism of the user at an ear concha of the user.

13. A control method of an electronic device that includes: an insertion portion configured to be at least partly inserted in an external ear canal of a user; a sensor configured to detect a signal relating to an organism of the user, in a state in which at least part of the insertion portion is inserted in the external ear canal of the user; and a driver unit configured to output sound from the insertion portion, the control method comprising
performing a predetermined process, based on a signal relating to the organism of the user detected by the sensor that satisfies a predetermined condition,
measuring a blood flow rate of the user, based on the signal relating to the organism of the user detected by the sensor that satisfies the predetermined condition,
determining a timing to output the sound based on a relationship between the measured blood flow rate of the user and a depth of sleep of humans, and
controlling the driver unit to output the sound at the determined timing.

14. A non-transitory computer-readable recording medium storing computer program instructions, which when executed by an electronic device that includes: an insertion portion configured to be at least partly inserted in an external ear canal of a user; a sensor configured to detect a signal relating to an organism of the user, in a state in which at least part of the insertion portion is inserted in the external ear canal of the user; and a driver unit configured to output sound from the insertion portion, cause a controller to
perform a predetermined process, based on a signal relating to the organism of the user detected by the sensor that satisfies a predetermined condition,
measure a blood flow rate of the user, based on the signal relating to the organism of the user detected by the sensor that satisfies the predetermined condition,
determine a timing to output the sound based on a relationship between the measured blood flow rate of the user and a depth of sleep of humans, and
control the driver unit to output the sound at the determined timing.

15. An electronic device comprising:
an insertion portion configured to be at least partly inserted in an external ear canal of a user;
a sensor configured to detect a signal relating to an organism of the user, in a state in which at least part of the insertion portion is inserted in the external ear canal of the user;
a driver unit configured to output sound from the insertion portion; and
a controller configured to perform a predetermined process, based on a signal relating to the organism of the user detected by the sensor that satisfies a predetermined condition,
wherein the controller is configured to measure a blood flow rate of the user, based on the signal relating to the organism of the user detected by the sensor that satisfies the predetermined condition,
the controller is configured to control the driver unit to output the sound at a timing determined based on the blood flow rate of the user, and
wherein the predetermined condition is a threshold set based on a history of signals detected by the sensor.

16. A system comprising:
an insertion portion configured to be at least partly inserted in an external ear canal of a user;
a sensor configured to detect a signal relating to an organism of the user, in a state in which at least part of the insertion portion is inserted in the external ear canal of the user;
a driver unit configured to output sound to the user; and
a controller configured to perform a predetermined process, based on a signal relating to the organism of the user detected by the sensor that satisfies a predetermined condition,
wherein the controller is configured to measure a blood flow rate of the user, based on the signal relating to the organism of the user detected by the sensor that satisfies the predetermined condition,
the controller is configured to determine a timing to output the sound based on a relationship between the measured blood flow rate of the user and a depth of sleep of humans, and
the controller is configured to control the driver unit to output the sound at the determined timing.

17. The system according to claim 16, wherein the insertion portion and the sensor are included in a device, and the driver unit is configured to output sound from the insertion portion.

18. The system according to claim 17, wherein the driver unit is included in the device.

19. A system comprising:
an insertion portion configured to be at least partly inserted in an external ear canal of a user;
a sensor configured to detect a signal relating to an organism of the user, in a state in which at least part of the insertion portion is inserted in the external ear canal of the user;
a driver unit configured to output sound to the user; and
a controller configured to perform a predetermined process, based on a signal relating to the organism of the user detected by the sensor that satisfies a predetermined condition,
wherein the controller is configured to measure a blood flow rate of the user, based on the signal relating to the organism of the user detected by the sensor that satisfies the predetermined condition, the controller is configured to control the driver unit to output the sound at a timing determined based on the blood flow rate of the user, and wherein the predetermined condition is a threshold set based on a history of signals detected by the sensor.

20. The system according to claim 19, wherein the insertion portion and the sensor are included in a device, and the driver unit is configured to output sound from the insertion portion.

21. The system according to claim 20, wherein the driver unit is included in the device.

* * * * *